(12) United States Patent
Baxter et al.

(10) Patent No.: US 8,846,954 B2
(45) Date of Patent: Sep. 30, 2014

(54) CRYSTALLISATION AND PURIFICATION OF GLYCOPYRRONIUM BROMIDE

(75) Inventors: Andrew Douglas Baxter, Cambridge (GB); Kenneth Walter Sinden, Essex (GB); Stefan Kleinebekel, Bielefeld (DE)

(73) Assignee: Sosei R&D Ltd., London (GB)

( * ) Notice: Subject to any disclaimer, the term of this patent is extended or adjusted under 35 U.S.C. 154(b) by 1556 days.

(21) Appl. No.: 11/817,166

(22) PCT Filed: Mar. 3, 2006

(86) PCT No.: PCT/GB2006/000770
§ 371 (c)(1),
(2), (4) Date: May 12, 2008

(87) PCT Pub. No.: WO2006/092617
PCT Pub. Date: Sep. 8, 2006

(65) Prior Publication Data
US 2008/0227988 A1    Sep. 18, 2008

(30) Foreign Application Priority Data
Mar. 3, 2005  (GB) .................................. 0504463.1

(51) Int. Cl.
*C07D 207/12*    (2006.01)
(52) U.S. Cl.
CPC .................................. *C07D 207/12* (2013.01)

USPC ........................................................ 548/556
(58) Field of Classification Search
CPC ...................................................... C07D 207/12
See application file for complete search history.

(56) References Cited

U.S. PATENT DOCUMENTS
2,956,062 A    10/1960    Lunsford

FOREIGN PATENT DOCUMENTS
WO    WO 98/21183    5/1998
WO    WO 2004/054971    7/2004

OTHER PUBLICATIONS
MethylBromide, http://www.google.com/search?sourceid=navclient&ie=UTF-8&oe=UTF-8&q=methyl+bromide+quarternary+solvent (2005).*

* cited by examiner

*Primary Examiner* — Sun Jae Yoo
(74) *Attorney, Agent, or Firm* — Saliwanchik, Lloyd & Eisenschenk

(57) ABSTRACT

A method for the production of crystalline glycopyrronium bromide, comprises the reaction of glycopyrronium base with methyl bromide in a solvent, in which the solvent is selected such that the diastereoisomeric ratio of the product favors the R,S and S,R diastereoisomers over the R,R, and S,S diastereoisomers, and separating the desired diastereoisomers by one or more controlled crystallization steps. This method gives a product having a particle size of narrow distribution.

9 Claims, No Drawings

CRYSTALLISATION AND PURIFICATION OF GLYCOPYRRONIUM BROMIDE

FIELD OF THE INVENTION

This invention relates to a method of crystallisation and purification of the anti-muscarinic drug glycopyrronium bromide.

BACKGROUND OF THE INVENTION

Glycopyrronium bromide (Glycopyrrolate, US Pharmacopeia) is the higher melting (193.2° C.-194.5° C.) of two possible diastereoisomeric racemates, i.e. the erythro racemate. Glycopyrronium bromide is manufactured by the method disclosed in U.S. Pat. No. 2,956,062, utilizing N-methylpyrrolidin-3-ol (NMP) and methyl hydroxycyclopentylmandelate (MCPM), as follows:

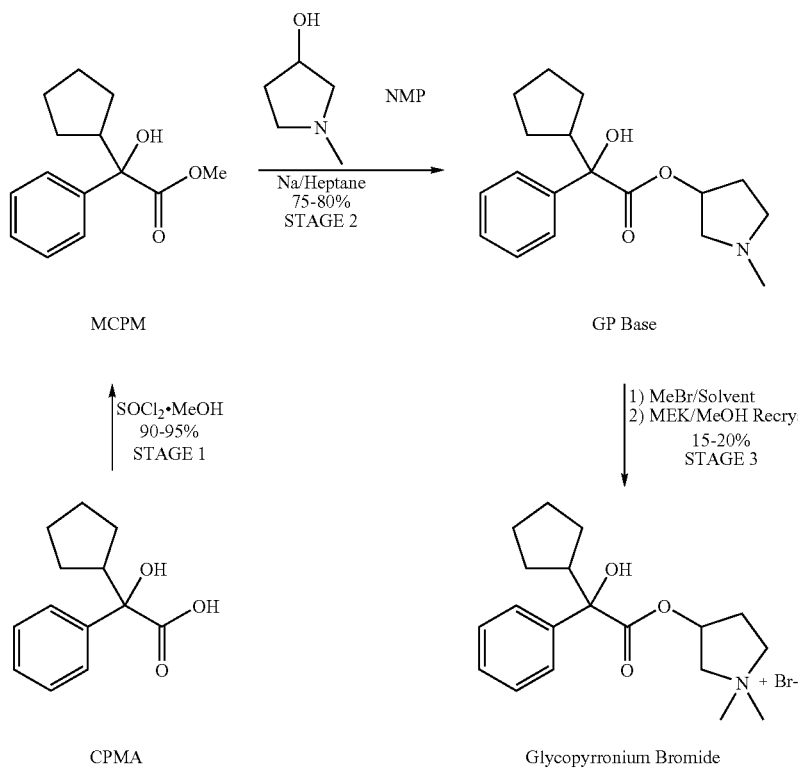

The initial product from the methylation reaction in methyl ethyl ketone (MEK; stage 3) is isolated as an approximately 50:50 mixture of the two possible pairs of diastereoisomers. In order to obtain the desired drug, i.e. the racemic mixture of the R,S and S,R pair of diastereoisomers, the R,R/S,S pair is removed by recrystallising the crude product from a mixture of methanol and MEK.

In the established manufacturing process, there is no provision to control the particle size of the drug substance. The large and inconsistent particle size produces a physically unstable drug substance following micronisation. Material is difficult to formulate into a drug product suitable for inhalation.

Further, apart from controlling the melting point, the US Pharmacopeia makes no provision for the determination of the amount of the R,R and S,S diastereoisomeric pair in the active pharmaceutical ingredient.

Commercially available MCPM may contain high levels of impurities. These impurities react competitively in stage 2, to produce high levels of carried through impurities in glycopyrronium base, and then in the final salt.

SUMMARY OF THE INVENTION

This invention relates to the production of glycopyrronium bromide utilising a novel crystallization process (Stage 3 in scheme 1). In addition to high purity, a consistent and fine particle size is controlled by the solvent, e.g. a solvent of the formula $R^1COR^2$ or $R^1COOR^2$ wherein $R^1$ and $R^2$ are each alkyl of 1 to 8 C atoms. In addition, the process preferably comprises also a slow cooling rate in the final crystallization steps. The particle size of glycopyrronium bromide produced by this method ensures a physically stable micronised drug substance that is suitable for formulation into a drug product optimized for inhaled delivery.

In a preferred embodiment of the invention, carrying out the methylation reaction in acetone ensures that the ratio of diastereoisomeric pairs is 60:40 in favour of the desired R,S and S,R pair. This ensures a reduction in the number of recrystallisation steps that are required to remove the R,R/S,S pair.

DESCRIPTION OF THE INVENTION

Based on information provided herein, one of ordinary skill in the art can readily determine a solvent that is suitable for use in the invention. While acetone is exemplified, other solvents that may be found suitable include esters, e.g. of acetic acid such as ethyl acetate, and other ketones such as methyl isobutyl ketone (MEK). In the given formulae, $R^1$ and $R^2$ are preferably $C_{1-4}$ alkyl, and $R^1$ is preferably methyl. A higher ketone than acetone is preferred for the recrystallisation.

Impurities are efficiently reduced by carrying out the methylation reaction in acetone compared to MEK. Sequential recrystallisations from MEK/methanol systematically eliminate these impurities alongside the R,R/S,S pair of diastereoisomers.

The overall yield of glycopyrronium bromide as a product of the methylation reaction and subsequent purification steps is typically 20-30%. Additional recrystallisation steps can be added should the material from the any given recrystallisation not meet the preferred specification of not more than 0.2% R,R/S,S.

The following Example (stage 3 of the 3-stage process shown above) illustrates the invention. "Cold" means a temperature of 0-10° C.

Stage 3: Methylation Reaction in Acetone

A solution of crude glycopyrronium base (13.0 kg; 42.8 mol) in acetone (130 L) is treated with methyl bromide gas (4.5 kg; 47.4 mol) over 30 minutes while maintaining a temperature between −5° C. and 5° C. The mixture is then warmed to between 15° C. and 25° C. and maintained at this temperature for 2 hours to ensure complete crystallisation of the glycopyrronium bromide has taken place. The product is filtered by centrifugation, washed with cold acetone (40-60 L) and collected (15 kg).

Stage 3.1: First Recrystallisation

The material (15 kg) is dissolved at reflux in a mixture of methanol (13.0 L) and MEK (90 L). Additional MEK (135 L) is added and reflux (75-85° C.) maintained for 30 minutes. The mixture is then cooled to between −10° C. and 0° C. at a rate of 30° C./hour, allowing controlled crystallisation of a purified product which is filtered by centrifugation, washed with cold MEK (30-50 L) and collected (7 kg). The purity of the product from this first recrystallisation is typically not less than 99% and the diastereoisomeric purity is typically 94-95% (by HPLC).

Stage 3.2: Second Recrystallisation

The material (7 kg) is dissolved at reflux in a mixture of methanol (10.2 L) and MEK (45 L). Additional MEK (65 L) is added and reflux (75-85° C.) maintained for 30 minutes. The mixture is then cooled to between −10° C. and 0° C. at a rate of 30° C./hour, allowing controlled crystallisation of a purified product which is filtered by centrifugation, washed with cold MEK (20-30 L) and the product collected (5.3 kg). The purity of the product from this recrystallisation is typically not less than 99.9% and the diastereoisomeric purity is typically not less than 99.5% (by HPLC).

Stage 3.3: Third Recrystallisation

The material (5.3 kg) is dissolved at reflux in a mixture of methanol (4.2 L) and MEK (33 L). Additional MEK (47 L) is added and reflux (75-85° C.) maintained for 30 minutes. The mixture is then cooled to between −10° C. and 0° C. at a rate of 30° C./hour allowing controlled crystallisation of a purified product that is filtered, washed with cold MEK (20 L) and oven dried. The drug substance is a fine white crystalline solid (4.9 kg). The purity of the product from this first recrystallisation is typically not less than 99.95% and the diastereoisomeric purity is typically not less than 99.8% (by HPLC).

Analytical Methods

This method uses a Waters Alliance 2695 HPLC system with a PDA 996 detector, column oven and Waters Empower data system or equivalent:

Column: Astec Cyclobond I 2000; 250 mm×4.6 mm ID
Temperature: 15° C.
Injection Volume: 20 μL
Detection: UV at 230 nM
Run Time: 20 min
Mobile Phase: 1.0 M triethyl ammonium acetate buffer solution (5.0 ml) mixed with acetonitrile (750 ml) and HPLC water (245 ml)
Flow Rate: 1.0 ml/min
Gradient: Isocratic Run times and relative response times for R,S/S,R glycopyrronium bromide (the drug substance) and the R,R/S,S impurity are as follows:

|  | Approx. Run Time (mins) | RRT |
|---|---|---|
| R,R/S,S | 10.3 | 0.95 |
| R,S/S,R | 10.8 | 1 |

The method has a limit of detection of 0.03% and a limit of quantification of 0.1%. The process as described is capable of reproducing a drug substance with not more than 0.2% of the R,R/S,S pair.

A HPLC method has been developed and validated providing an in-process check and test method to control levels of this impurity to <0.2% in batches of the drug substance. Due to the efficiency of the crystallization required to meet this specification, all other impurities are eliminated. Impurities carried through from impure MCPM can readily be eliminated in the recrystallisation steps.

| Stage 1, Purity of MCPM | | | |
|---|---|---|---|
| Batch | GC purity | Impurity 1 | Impurity 2 |
| MCPM | 76.8% | 15.9% | 3.2% |

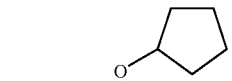

Impurity 1

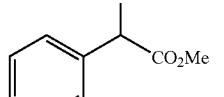

Impurity 2

| Stage 2, Glycopyrronium Base Formation from impure MCPM | | | |
|---|---|---|---|
| Yield | HPLC Purity | No of Imp >0.1% | Impurity 1.1 |
| 8.2 kg (54%) | 89.7% | 4 | 8.2% |
| 5.3 kg (36%) | 95.2% | 7 | 2.8% |

Stage 2, Glycopyrronium Base Formation from impure MCPM

| Yield | HPLC Purity | No of Imp >0.1% | Impurity 1.1 |
|---|---|---|---|

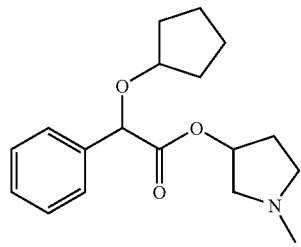

Impurity 1.1

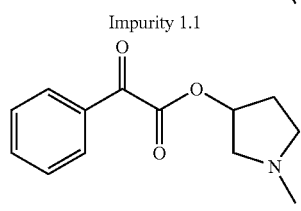

Impurity 2.1

Stage 3, Glycopyrronium Bromide Formation and Purification.

| Stage | Yield | HPLC | RS,SR | RR,SS | Imp 1.2 | Imp 2.2 |
|---|---|---|---|---|---|---|
| 3 | 18 kg | 98.0% | 61.6 | 38.4 | 1.1 | 0.5 |
| 3.1 | 7 kg | 99.5% | 94.2 | 5.8 | 0.4 | ND |
| 3.2 | 5.3 kg | 99.9% | 99.6 | 0.4 | 0.1 | ND |
| 3.3 | 4.9 kg (29.6%) | 99.96% | >99.8 | <0.2 | ND | ND |

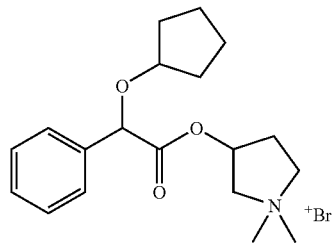

Impurity 1.2

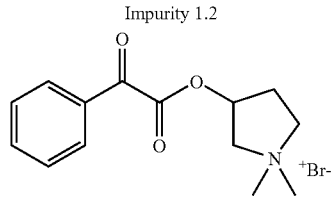

Impurity 2.2

ND = Not Detected

This Example validates the purification procedure, demonstrating that even poor quality MCPM can be processed to drug substance of excellent quality. The elimination of these impurities is apparently the consequence of controlled recrystallisation. Uncontrolled crystallization leads to an impure product with an inconsistent particle size distribution. It was surprising to find the controlled cooling rate employed not only defined a high level of purity but also provided control of particle size distribution and uniform morphological habit, as shown by imaging. Subsequent micronisation of this product has provided a physically stable drug substance that is suitable for formulation into a drug product optimized for inhaled delivery.

The invention claimed is:

1. A method for the production of crystalline glycopyrronium bromide in the form of predominantly the R,S and S,R diastereoisomers with respect to the R,R, and S,S diastereoisomers, which comprises reacting glycopyrronium base, in acetate acetone, with methyl bromide and then separating the desired diastereoisomers by a controlled crystallization step conducted in a solvent comprising the same or different compounds of the formula $R^1COR^2$ or $R^1COOR^2$ wherein $R^1$ and $R^2$ are independently $C_{1-8}$ alkyl, wherein the diastereoisomeric ratio of the glycopyrronium bromide is at least 60:40 in favour of the R,S/S,R-pair.

2. The method according to claim 1, wherein the crystallisation solvent comprises a ketone of the formula $R^1COR^2$.

3. The method according to claim 2, wherein the crystallisation solvent comprises a higher ketone than acetone.

4. The method according to claim 3, wherein the crystallisation solvent comprises methyl ethyl ketone or methyl isobutyl ketone.

5. The method according to claim 4, wherein the crystallisation solvent is a mixture of methyl ethyl ketone and methanol.

6. The method according to claim 1, wherein the particle size of the product is less than 100 µm.

7. The method according to claim 6, wherein the particle size is less than 50 µm.

8. The method according to claim 1, further comprising one or more additional controlled crystallization steps conducted in a solvent comprising the same or different compounds of the formula $R^1COR^2$ or $R^1COOR^2$ wherein $R^1$ and $R^2$ are independently $C_{1-8}$ alkyl.

9. The method according to claim 8, wherein the diastereoisomeric purity of the product is more than 99.8% R,S/S,R.

* * * * *